United States Patent
Inoue

(10) Patent No.: US 9,804,071 B2
(45) Date of Patent: Oct. 31, 2017

(54) SAMPLE COOLING DEVICE, AUTOSAMPLER PROVIDED WITH THE SAME, AND SAMPLE COOLING METHOD

(71) Applicant: SHIMADZU CORPORATION, Kyoto-shi, Kyoto (JP)

(72) Inventor: Takashi Inoue, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 0 days.

(21) Appl. No.: 14/759,105

(22) PCT Filed: Mar. 18, 2013

(86) PCT No.: PCT/JP2013/057605
§ 371 (c)(1),
(2) Date: Jul. 2, 2015

(87) PCT Pub. No.: WO2014/147696
PCT Pub. Date: Sep. 25, 2014

(65) Prior Publication Data
US 2015/0355061 A1 Dec. 10, 2015

(51) Int. Cl.
*F25D 21/04* (2006.01)
*G01N 1/42* (2006.01)
(Continued)

(52) U.S. Cl.
CPC .................. *G01N 1/42* (2013.01); *B01L 7/00* (2013.01); *F25B 47/006* (2013.01); *F25D 21/04* (2013.01);
(Continued)

(58) Field of Classification Search
CPC .... B01L 2300/10; F25B 47/006; F25D 21/04; F25D 2317/0411; F25D 2317/04111
See application file for complete search history.

(56) References Cited

U.S. PATENT DOCUMENTS 6,170,267 B1  1/2001  Kitaoka
2010/0077775 A1*  4/2010  Smith ............... F25D 17/042
62/93

FOREIGN PATENT DOCUMENTS

JP   62-186137 A   8/1987
JP   1-266481 A   10/1989
(Continued)

OTHER PUBLICATIONS

International Written Opinion of PCT/JP2013/057605, dated Apr. 23, 2013. [PCT/ISA/237].

(Continued)

*Primary Examiner* — Justin Olamit
(74) *Attorney, Agent, or Firm* — Sughrue Mion, PLLC

(57) ABSTRACT

There are provided a sample cooling device capable of effectively removing moisture in the air inside an accommodating chamber where a sample container is accommodated, and of preventing a problem caused by occurrence of frost, an autosampler provided with the same, and a sample cooling method. A first driving process of setting a set temperature of a dehumidifier section to at or below the freezing point, and a second driving process of stopping driving of the dehumidifier section or of raising the set temperature of the dehumidifier section to above the freezing point after the first driving process is performed over a predetermined period of time are performed. Thus, the set temperature of the dehumidifier section may be made to at or below the freezing point by the first driving process, and moisture in the air inside the accommodating chamber may be made to temporarily attach to the dehumidifier section as frost and then be melted by the second driving process and be collected as water.

5 Claims, 3 Drawing Sheets

(51) Int. Cl.
*F25B 47/00* (2006.01)
*B01L 7/00* (2006.01)
*G01N 35/10* (2006.01)
*G01N 30/24* (2006.01)
*G01N 35/00* (2006.01)

(52) U.S. Cl.
CPC .. *G01N 35/1095* (2013.01); *B01L 2300/0663* (2013.01); *B01L 2300/10* (2013.01); *B01L 2300/1894* (2013.01); *G01N 30/24* (2013.01); *G01N 2035/00445* (2013.01)

(56) References Cited

FOREIGN PATENT DOCUMENTS

JP  2000-74801 A  3/2000
JP  2000-74802 A  3/2000

OTHER PUBLICATIONS

Communication dated Apr. 26, 2016 from Japanese Patent Office in counterpart Application No. 2015-506384.
International Search Report of PCT/JP2013/057605, dated Apr. 23, 2013. [PCT/ISA/210].
Communication dated Jan. 10, 2017 from Japanese Patent Office in counterpart Application No. 2015-506384.

* cited by examiner

… (1)

SAMPLE COOLING DEVICE, AUTOSAMPLER PROVIDED WITH THE SAME, AND SAMPLE COOLING METHOD

CROSS REFERENCE TO RELATED APPLICATIONS

This application is a National Stage of International Application No. PCT/JP2013/057605 filed Mar. 18, 2013, the contents of all of which are incorporated herein by reference in their entirety.

TECHNICAL FIELD

The present invention relates to a sample cooling device for cooling a sample in a sample container that is accommodated in an accommodating chamber, an autosampler provided with the same, and a sample cooling method.

BACKGROUND ART

For example, some analysis devices such as a liquid chromatograph are provided with an autosampler for sucking a sample in a sample container by a needle and for automatically analyzing the sample. Depending on the type of sample to be the analysis target, the sample may sometimes have to be cooled from the standpoint of preventing alteration. In such a case, the sample in the sample container may be cooled by using a sample cooling device (for example, see Patent Document 1).

Regarding the sample cooling device, a direct cooling type and an air cooling type are known, for example. According to a direct-cooling sample cooling device, for example, a plurality of sample containers are accommodated in a highly thermal conductive rack and the rack is installed in a cooling section so that the sample containers on the rack may be cooled by a cooler such as a Peltier device provided to the cooling section. That is, with the direct-cooling sample cooling device, the cooling section configures an installation section for installing the sample containers. On the other hand, according to an air-cooling sample cooling device, a sample container may be cooled by air, by cooling the air inside an accommodating chamber accommodating the sample container by a cooler.

Prior Art Documents

Patent Documents

JP 2000-74802 A

SUMMARY OF THE INVENTION

Problems to be Solved by the Invention

With a sample cooling device as described above, moisture in the air inside an accommodating chamber where a sample container is accommodated may be condensed at the time of cooling of a sample, and the moisture may negatively affect analysis of the sample. For example, if moisture is condensed on a sample container at an autosampler, the moisture on the sample container possibly gets mixed in the sample at the time of insertion of a needle into the sample container, thereby changing the concentration of the sample.

To suppress such a problem caused by condensation, a sample cooling device disclosed in Patent Document 1 adopts a structure where dehumidification is performed by cooling the air inside the accommodating chamber. Specifically, by causing the set temperature of a dehumidifier section to be near the dew point, the moisture in the air inside the accommodating chamber is condensed at the dehumidifier section, and the absolute humidity inside the accommodating chamber may be reduced.

However, with a conventional technique as described above, if the cooling temperature of a sample is low, a problem caused by condensation may not be sufficiently suppressed. That is, in a case where the cooling temperature of a sample is around the dew point (for example, about 4° C.), there is a problem that, even if dehumidification is performed with the set temperature of the dehumidifier section being near the dew point, moisture is condensed at not only the dehumidifier section but also around the cooling section (such as at the sample container).

Thus, it is conceivable to set the set temperature of the dehumidifier section at a temperature lower than the dew point, but if the set temperature of the dehumidifier section is too low, frost may attach to the dehumidifier section, and the frost may negatively affect the dehumidification function. Also, if a large amount of frost is attached to the dehumidifier section, a task of removing the frost has to be performed, and if the task is not performed, the frost may naturally melt and the inside of the device may be flooded with water.

The present invention has been made in view of the above circumstances, and has its object to provide a sample cooling device capable of effectively removing moisture in the air inside an accommodating chamber accommodating a sample container and of preventing a problem that is caused by occurrence of frost, an autosampler provided with the same, and a sample cooling method.

Means for Solving the Problems

A sample cooling device of the present invention is a sample cooling device for cooling a sample in a sample container that is accommodated in an accommodating chamber, the sample cooling device including: a cooling section configured to cool the sample container that is accommodated in the accommodating chamber; a dehumidifier section configured to perform dehumidification by cooling air inside the accommodating chamber; and a control section configured to control driving of the dehumidifier section, wherein the control section performs a first driving process of setting a set temperature of the dehumidifier section to at or below a freezing point, and a second driving process of stopping driving of the dehumidifier section or of raising the set temperature of the dehumidifier section to above the freezing point after the first driving process is performed over a predetermined period of time.

According to such a configuration, the set temperature of the dehumidifier section may be set to at or below the freezing point by the first driving process, and moisture in the air inside the accommodating chamber may be made to temporarily attach to the dehumidifier section as frost, and then the frost may be melted by the second driving process and be collected as water. Accordingly, even if the cooling temperature of a sample at the cooling section is relatively low, since the dehumidifier section is set to an even lower temperature, moisture may be prevented from being condensed around the cooling section.

Particularly, since dehumidification may be performed more efficiently in a case where moisture is made to attach to the dehumidifier section as frost than in a case where it is condensed, moisture in the air inside the accommodating chamber where the sample container is accommodated may be effectively removed. Also, by melting by the second driving process the frost which was attached to the dehumidifier section in the first driving process, problems caused by occurrence of frost may be prevented.

The control section may alternately repeat the first driving process and the second driving process.

According to such a configuration, by repeatedly performing the operation of causing moisture in the air inside the accommodating chamber to attach to the dehumidifier section as frost in the first driving process, and melting the frost by the second driving process, dehumidification may be performed over a plurality of times. It is thereby possible to prevent a large amount of frost from attaching to the dehumidifier section or the cooling temperature of a sample at the cooling section from being negatively affected, due to the set temperature of the dehumidifier section being at or below the freezing point over a long period of time.

Moreover, also in a case where the humidity in the accommodating chamber changes such as when the accommodating chamber is temporarily opened in mid-course and is closed again, moisture in the air inside the accommodating chamber may be reliably removed by the configuration where the first driving process and the second driving process are alternately repeated.

The cooling section may configure an installation section for installing the sample container.

According to such a configuration, a sample in the sample container may be efficiently and desirably cooled at the direct-cooling sample cooling device where the cooling section configures the installation section for installing the sample container. With such a direct-cooling sample cooling device, moisture tends to condense around the cooling section, but according to the present invention, condensation of moisture around the cooling section may be effectively prevented.

An autosampler of the present invention includes: the sample cooling device; and a suction mechanism configured to suck a sample inside the sample container that is accommodated in the accommodating chamber.

According to such a configuration, the sample cooling device capable of effectively preventing condensation of moisture around the cooling section may be adopted by an autosampler, and thus it is possible to prevent moisture that is condensed on the sample container from getting mixed in the sample at the time of sucking the sample in the sample container, and to prevent occurrence of a problem such as the concentration of the sample being changed.

A sample cooling method of the present invention is for performing dehumidification by cooling air inside an accommodating chamber by a dehumidifier section while cooling a sample in a sample container that is accommodated in the accommodating chamber by a cooling section, the method includes: a first driving process step of setting a set temperature of the dehumidifier section to at or below a freezing point; and a second driving process step of stopping driving of the dehumidifier section or of raising the set temperature of the dehumidifier section to above the freezing point after the first driving process step is performed over a predetermined period of time.

Effects of the Invention

According to the present invention, moisture in the air inside the accommodating chamber where the sample container is accommodated may be effectively removed by causing the moisture to attach to the dehumidifier section as frost by the first driving process, and also, problems caused by occurrence of frost may be prevented by melting by the second driving process the frost which was attached to the dehumidifier section in the first driving process.

MODE FOR CARRYING OUT THE INVENTION

Figure 1:
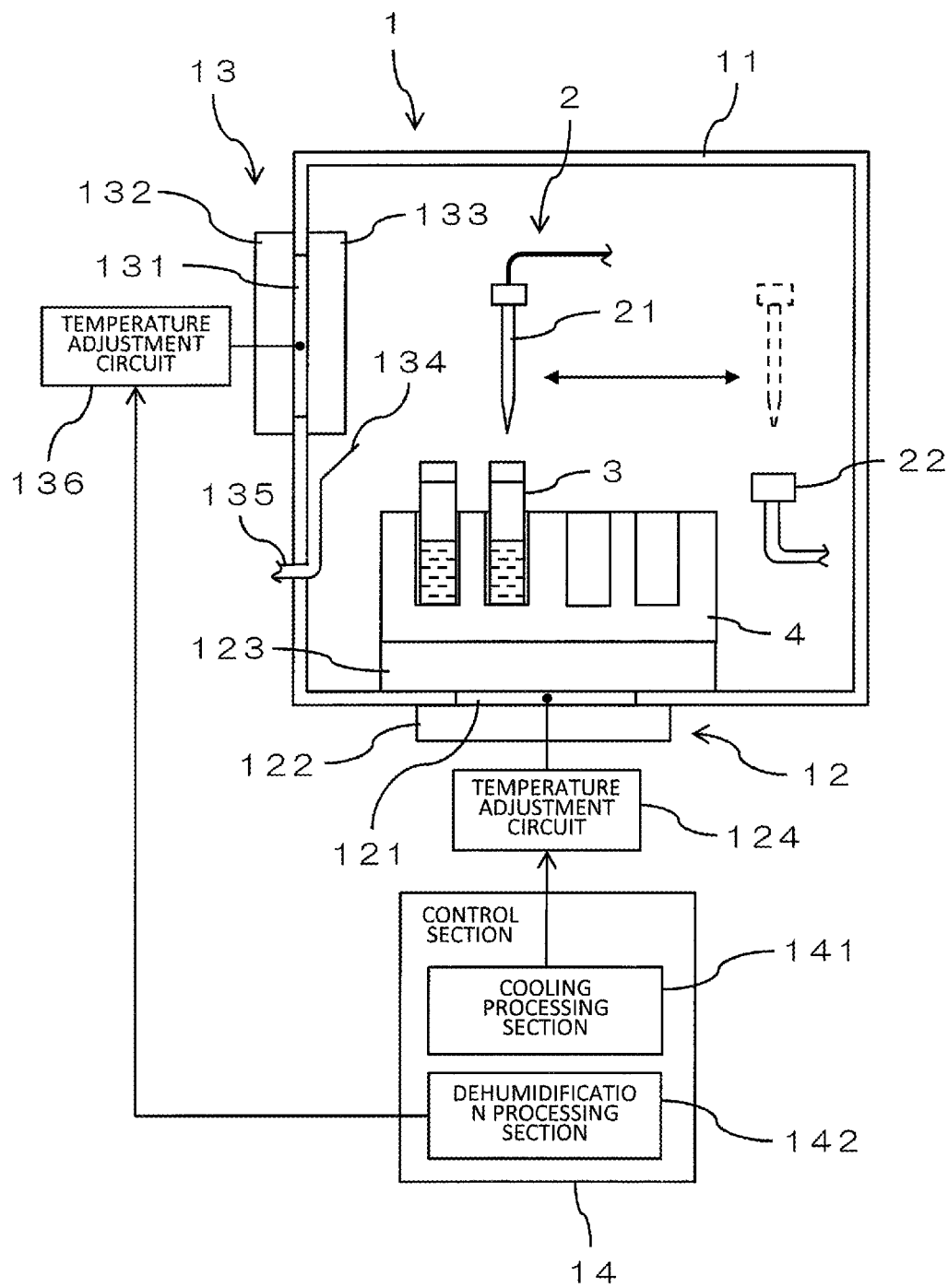
FIG. 1 is a diagram showing an example configuration of an autosampler according to an embodiment of the present invention.

FIG. 1 is a diagram showing an example configuration of an autosampler according to an embodiment of the present invention. FIG. 1 shows a schematic cross-sectional diagram of a specific configuration of main sections of an autosampler, and also shows a block diagram of the electrical configuration. This autosampler may be applied to various analysis devices such as a liquid chromatograph, for example.

The autosampler according to the present embodiment includes a sample cooling device 1 for cooling a sample, and a suction mechanism 2 for sucking the sample that is being cooled by the sample cooling device 1. The sample is contained in a sample container 3 such as a vial, and a plurality of the sample containers 3 may be installed inside the sample cooling device 1 by being held by a rack 4. The rack 4 is formed of a highly thermal conductive metal, for example.

The sample cooling device 1 includes an accommodating chamber 11, a cooling section 12, a dehumidifier section 13, a control section 14, and the like, for example. The accommodating chamber 11 has its wall surface formed of a highly heat insulating material, for example, and the accommodating chamber 11 may be hermetically sealed while accommodating inside the sample container 3 together with the rack 4. By cooling the sample container 3 that is accommodated in the accommodating chamber 11, the sample in the sample container 3 may be cooled.

The cooling section 12 is for cooling the sample container 3 that is accommodated in the accommodating chamber 11, and includes a Peltier device 121, a heat sink fin 122, an installation section 123, a temperature adjustment circuit 124, and the like, for example. The Peltier device 121 is provided in such a way as to partition the inside and the outside of the accommodating chamber 11, and for example, the heat sink fin 122 is attached on the Peltier device 121, on the surface on the outside of the chamber (the lower side), and the installation section 123 is attached on the Peltier device 121, on the surface on the inside of the chamber (the upper side).

The installation section 123 is formed of a highly thermal conductive metal, for example, and the rack 4 may be installed above the installation section 123. The installation section 123 may thereby be cooled by the Peltier device 121, and the sample container 3 on the rack 4 may be cooled through the installation section 123. At this time, the heat that is absorbed by the Peltier device 121 from the installation section 123 is radiated outside the accommodating chamber 11 via the heat sink fin 122.

The temperature adjustment circuit 124 adjusts the temperature of the cooling section 12 by changing the energization state of the Peltier device 121. Specifically, the energization state of the Peltier device 121 is changed by the temperature adjustment circuit 124 in such a way that the temperature of the installation section 123 gets closer to a set temperature (a cooling temperature), while the temperature of the installation section 123 is being detected by a temperature sensor (not shown).

In this manner, in the present embodiment, the cooling section 12 configures the installation section 123 where the sample container 3 is to be installed. That is, the sample cooling device 1 according to the present embodiment is a direct cooling type, and by installing the rack 4 at the cooling section 12, the sample container 3 on the rack 4 may be cooled.

The dehumidifier section 13 is for performing dehumidification by cooling the air inside the accommodating chamber 11, and includes a Peltier device 131, a heat sink fin 132, an attachment section 133, a tray 134, a drainpipe 135, a temperature adjustment circuit 136, and the like, for example. The Peltier device 131 is provided in such a way as to partition the inside and the outside of the accommodating chamber 11, and for example, the heat sink fin 132 is attached on the Peltier device 131, on the surface on the outside of the chamber, and the attachment section 133 is attached on the Peltier device 131, on the surface on the inside of the chamber.

The attachment section 133 is formed of a highly thermal conductive metal, for example, and as with the heat sink fin 132, it may be formed into a fin shape where a plurality of metal plates are arranged in parallel. In this case, the plurality of metal plates forming the attachment section 133 are provided each preferably extending in the vertical direction. At the time of dehumidification of the inside of the accommodating chamber 11, the attachment section 133 is cooled by the Peltier device 131. At this time, the heat absorbed by the Peltier device 131 from the attachment section 133 is radiated outside the accommodating chamber 11 through the heat sink fin 132.

The tray 134 is for collecting water produced at the time of dehumidification, and is enabled to receive water running down on the attachment section 133 by being arranged below the attachment section 133. Water collected in the tray 134 is drained outside the accommodating chamber 11 via the drainpipe 135.

The temperature adjustment circuit 136 adjusts the temperature of the dehumidifier section 13 by changing the energization state of the Peltier device 131. Specifically, the energization state of the Peltier device 131 is changed by the temperature adjustment circuit 136 in such a way that the temperature of the attachment section 133 gets closer to a set temperature, while the temperature of the attachment section 133 is being detected by a temperature sensor (not shown).

The control section 14 is a configuration including a CPU (Central Processing Unit), for example, and functions as various functional sections such as a cooling processing section 141, a dehumidification processing section 142 and the like by the CPU executing programs. The cooling processing section 141 performs a process of controlling driving of the cooling section 12 (the temperature adjustment circuit 124). On the other hand, the dehumidification processing section 142 performs a process of controlling driving of the dehumidifier section 13 (the temperature adjustment circuit 136).

The suction mechanism 2 is provided with a needle 21 that is to be inserted into the sample container 3. The needle 21 is configured to be able to move in the horizontal and vertical directions, and is inserted into the sample container 3 by being horizontally moved to above the sample container 3 and then moved downward, and the sample inside the sample container 3 is sucked from the needle 21. Then, the needle 21 is moved upward to be removed outside the sample container 3, and is horizontally moved to a sample injection port 22. Then, the sample sucked out from the sample container 3 is injected into the sample injection port 22, and automatic supply of a predetermined amount of sample for analysis is thereby enabled.

Figure 2:
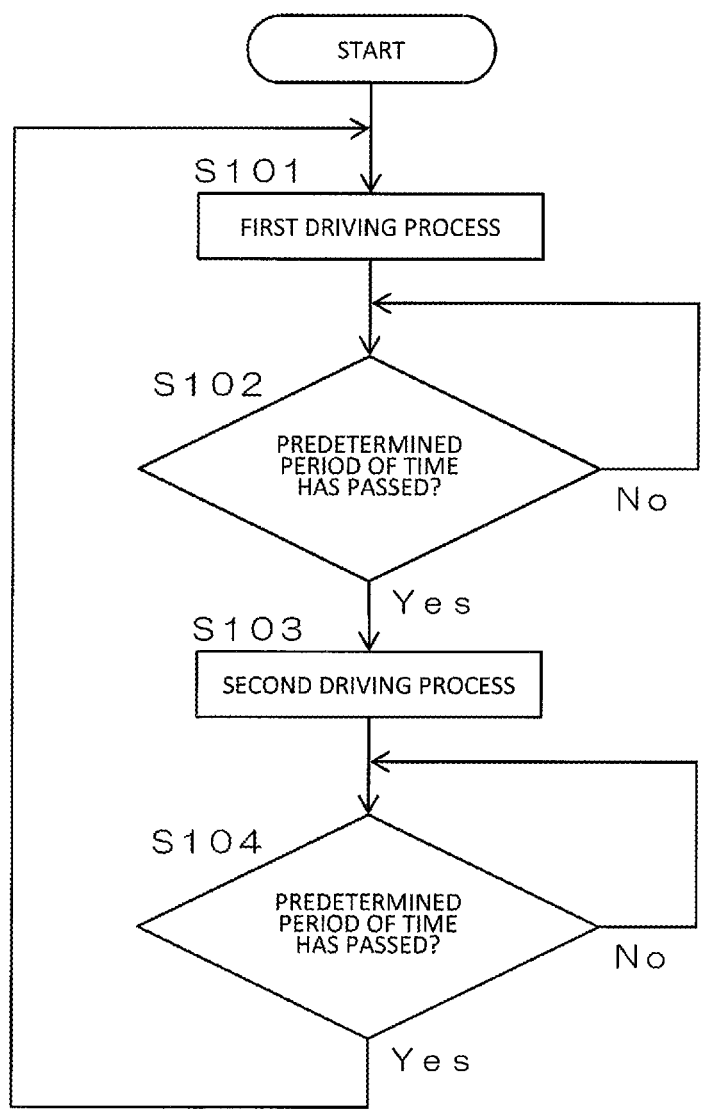
FIG. 2 is a flow chart showing an example of a process by a dehumidification processing section of a control section.
Figure 3:
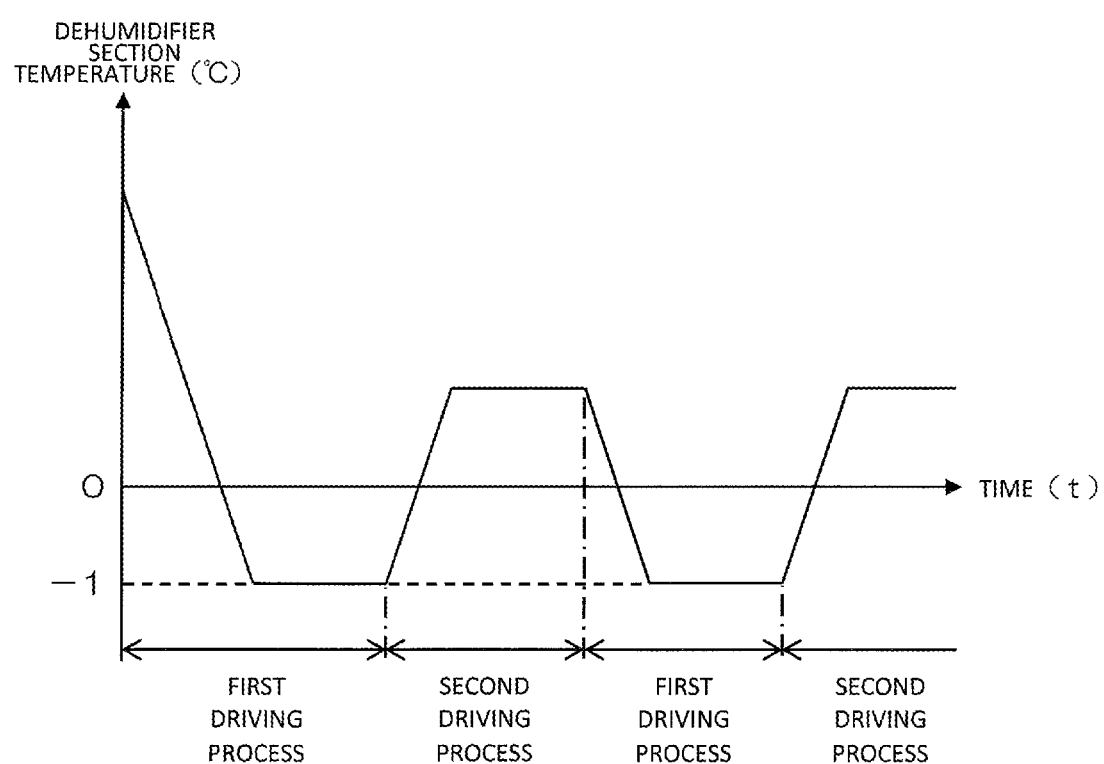
FIG. 3 is a diagram showing an example of temperature change at a dehumidifier section at the time of dehumidification of the inside of an accommodating chamber.

FIG. 2 is a flow chart showing an example of a process by the dehumidification processing section 142 of the control section 14. Also, FIG. 3 is a diagram showing an example of temperature change at the dehumidifier section 13 at the time of dehumidification of the inside of the accommodating chamber 11. In the following, an example of a mode of dehumidification of the inside of the accommodating chamber 11 will be described with reference to FIGS. 2 and 3.

At the time of dehumidifying the inside of the accommodating chamber 11, first, a first driving process is performed by setting the set temperature of the dehumidifier section 13 to at or below the freezing point (for example, −1° C.) (step S101: a first driving process step). The temperature of the attachment section 133 of the dehumidifier section 13 located inside the accommodating chamber 11 is gradually reduced by this first driving process, and when the temperature of the attachment section 133 reaches or falls below the freezing point, the moisture in the air inside the accommodating chamber 11 attaches to the attachment section 133 as frost. The absolute humidity inside the accommodating chamber 11 may thereby be reduced.

The first driving process is performed over a predetermined period of time that is long enough to cause moisture in the air inside the accommodating chamber 11 to attach to the attachment section 133 as frost. In the present embodiment, for example, the first driving process is performed until a specific period of time has passed after the temperature of the attachment section 133 has reached or fallen below the freezing point, by detecting the temperature of the attachment section 133 by a temperature sensor. However, such a configuration is not restrictive, and any period of time may be set as the predetermined period of time mentioned above; for example, a configuration is possible where the first driving process is performed until a specific period of time has passed after the start of the first driving process.

After the first driving process is performed over the predetermined period of time (Yes in step S102), a second driving process for melting the frost attached to the attachment section 133 is performed (step S103: a second driving process step). This second driving process may be realized by stopping driving of the dehumidifier section 13 or by raising the set temperature of the dehumidifier section to above the freezing point, for example.

That is, frost attached to the attachment section 133 may be melted by causing the temperature of the attachment section 133 of the dehumidifier section 13 to which frost was attached by the first driving process to gradually increase by the second driving process and to transition to a temperature higher than the freezing point. Water that is produced by melting of the frost falls into the tray 134 along the attachment section 133, and is drained outside the accommodating chamber 11 through the drainpipe 135.

The second driving process is performed over a predetermined period of time that is long enough to melt the frost attached to the attachment section 133. In the present embodiment, for example, the second driving process is performed until a specific period of time has passed after the temperature of the attachment section 133 was raised to above the freezing point, by detecting the temperature of the attachment section 133 by a temperature sensor. However, such a configuration is not restrictive, and any period of time may be set as the predetermined period of time mentioned above; for example, a configuration is possible where the second driving process is performed until a specific period of time has passed after the start of the second driving process.

In this manner, in the present embodiment, the set temperature of the dehumidifier section 13 may be set to at or below the freezing point by the first driving process, and moisture in the air inside the accommodating chamber 11 may be made to temporarily attach to the dehumidifier section as frost, and then the frost may be melted by the second driving process and be collected as water. Accordingly, even if the cooling temperature of a sample at the cooling section 12 is relatively low (for example, about 4° C.), since the dehumidifier section 13 is set to an even lower temperature, moisture may be prevented from being condensed around the cooling section 12.

Particularly, since dehumidification may be performed more efficiently in a case where moisture is made to attach to the dehumidifier section 13 as frost than in a case where it is condensed, moisture in the air inside the accommodating chamber 11 where the sample container 3 is accommodated may be effectively removed. Also, by melting by the second driving process the frost which was attached to the dehumidifier section 13 in the first driving process, problems caused by occurrence of frost may be prevented.

Also, the sample cooling device 1 that is capable of effectively preventing condensation of moisture around the cooling section 12 may be adopted by an autosampler, and thus it is possible to prevent moisture that is condensed on the sample container 3 from getting mixed in the sample at the time of sucking the sample in the sample container 3 (for example, at the time of inserting the needle 21 into the sample container 3), and to prevent occurrence of a problem such as the concentration of the sample being changed.

In the present embodiment, after the second driving process is performed over the predetermined period of time (Yes in step S104), the first driving process is performed again (step S101). That is, the first driving process (step S101) and the second driving process (step S102) are alternately repeated. Accordingly, as shown in FIG. 3, a period of time when the temperature of the dehumidifier section 13 (the attachment section 133) is at or below the freezing point and a period of time when it is above the freezing point are alternately repeated.

In this manner, by repeatedly performing the operation of causing moisture in the air inside the accommodating chamber 11 to attach to the dehumidifier section 13 as frost in the first driving process, and melting the frost by the second driving process, dehumidification may be performed over a plurality of times. It is thereby possible to prevent a large amount of frost from attaching to the dehumidifier section 13 (the attachment section 133) or the cooling temperature of a sample at the cooling section 12 from being negatively affected, due to the set temperature of the dehumidifier section 13 being at or below the freezing point over a long period of time.

Moreover, also in a case where the humidity in the accommodating chamber 11 changes such as when the accommodating chamber 11 is temporarily opened in mid-course and is closed again, moisture in the air inside the accommodating chamber 11 may be reliably removed by the configuration where the first driving process and the second driving process are alternately repeated.

Particularly, in the present embodiment, a sample in the sample container 3 may be efficiently and desirably cooled at the direct-cooling sample cooling device 1 where the cooling section 12 configures the installation section 123 for installing the sample container 3. With such a direct-cooling sample cooling device 1, moisture tends to condense around the cooling section 12, but according to the configuration of the present embodiment, condensation of moisture around the cooling section 12 may be effectively prevented.

In the embodiment described above, a configuration where the first driving process and the second driving process are alternately repeated is described. However, such a configuration is not restrictive, and a configuration where the first driving process and the second driving process are each performed once is also possible. With a configuration where the accommodating chamber 11 is hermetically closed at all times during operation of the autosampler, if dehumidification inside the accommodating chamber 11 is performed once, the humidity inside the accommodating chamber 11 is not increased thereafter, and thus it is sufficient to perform each of the first driving process and the second driving process just once.

The set temperature of the dehumidifier section 13 at the time of the first driving process is not limited to −1° C., and may be set to any value at or below the freezing point. Furthermore, also in the case of setting the set temperature of the dehumidifier section 13 to above the freezing point at the time of the second driving process, the set temperature of the dehumidifier section 13 may be set to any value above the freezing point.

Moreover, in the embodiment described above, the direct-cooling sample cooling device 1 where the cooling section 12 configures the installation section 123 for installing the sample container 3 is described. However, such a configuration is not restrictive, and the present invention may also be applied to an air-cooling sample cooling device that cools the sample container 3 by air.

The sample container 3 is not limited to be cooled while being held by the rack 4, and it may also be cooled while being directly installed in the installation section 123, for example. Also, the Peltier device 121 for cooling the sample container 3 at the cooling section 12, and the Peltier device 131 for cooling the air at the dehumidifier section 13 are both replaceable by a different cooler.

It is possible to provide a program for causing a computer to function as the sample cooling device or the autosampler as described above. In this case, the program may be provided being stored in a storage medium, or the program itself may be provided.

DESCRIPTION OF REFERENCE SIGNS

1 sample cooling device
2 suction mechanism
3 sample container
4 rack
11 accommodating chamber
12 cooling section
13 dehumidifier section
14 control section
21 needle
22 sample injection port
121 Peltier device
122 heat sink fin
123 installation section 124 temperature adjustment circuit
131 Peltier device
132 heat sink fin
133 attachment section
134 tray
135 drainpipe
136 temperature adjustment circuit
141 cooling processing section
142 dehumidification processing section

The invention claimed is:

1. A sample cooling device for cooling a sample in a sample container comprising:
   a sample in a sample container, the sample container being accommodated in an accommodating chamber;
   a cooling section in direct contact with the sample container and configured to perform a cooling process to cool the sample container;
   a dehumidifier section configured to perform a dehumidification process by cooling air inside the accommodating chamber; and
   a control section configured to control driving of the dehumidifier section,
   wherein the control section performs a first driving process of setting a set temperature of the dehumidifier section to a temperature which is lower than a temperature of the sample container being cooled by the cooling section during operation of the dehumidifier section, and a second driving process of stopping driving of the dehumidifier section or of raising the set temperature of the dehumidifier section to above the set temperature at a time of the first driving process after the first driving process is performed over a predetermined period of time,
   wherein the dehumidification process and the cooling process begin simultaneously.

2. The sample cooling device according to claim 1, wherein the control section alternately repeats the first driving process and the second driving process.

3. The sample cooling device according to claim 1, wherein the cooling section is a direct-cooling device that includes an installation section for installing the sample container.

4. An autosampler comprising:
   the sample cooling device according to claim 1, and
   a suction mechanism configured to suck a sample inside the sample container that is accommodated in the accommodating chamber.

5. A sample cooling method for cooling a sample in a sample container, the method comprising:
   a dehumidification step of cooling air inside an accommodating chamber by a dehumidifier section;
   a cooling step of cooling a sample in the sample container that is accommodated in the accommodating chamber by a cooling section, in direct contact with the sample container;
   a first driving process step of setting a set temperature of the dehumidifier section to or below a freezing point; and
   a second driving process step of stopping driving of the dehumidifier section or of raising the set temperature of the dehumidifier section to above the freezing point after the first driving process step is performed over a predetermined period of time,
   wherein the dehumidification step and the cooling step begin simultaneously.

* * * * *